Figure 1:
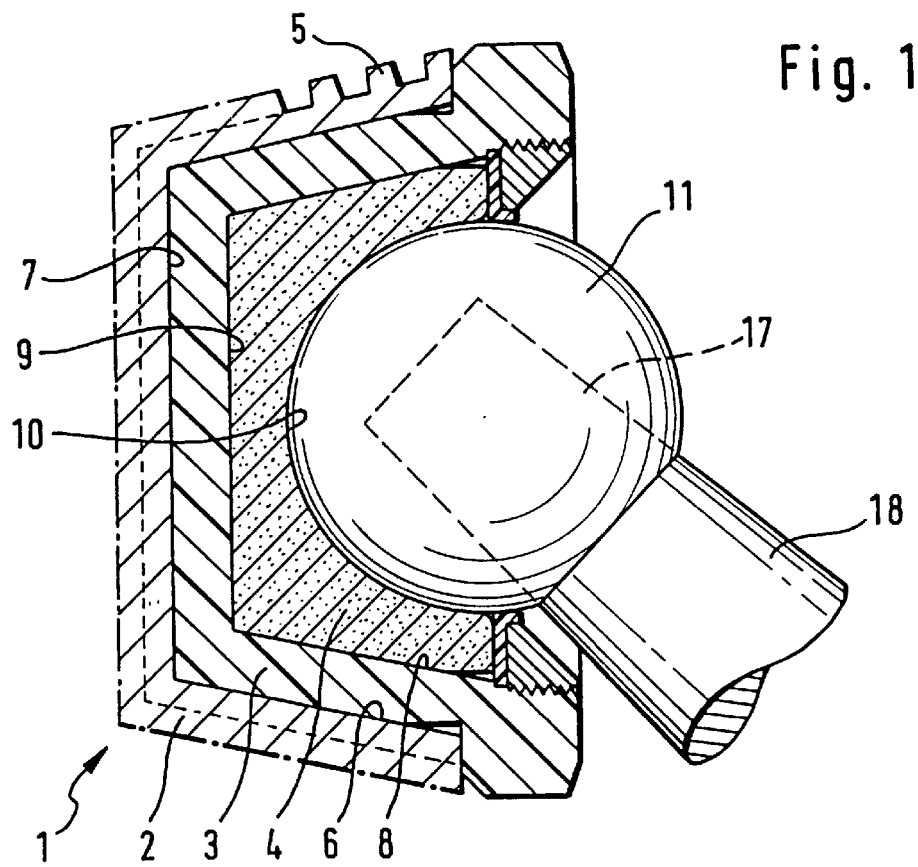

United States Patent
Keller et al.

[11] Patent Number: 6,096,083
[45] Date of Patent: *Aug. 1, 2000

[54] ENDOPROSTHESIS WITH A BALL-AND-SOCKET JOINT

[75] Inventors: Arnold Keller, Kayhude; Philipp Lubinus, Kiel, both of Germany

[73] Assignee: Waldemar Link (GmbH & Co.), Hamburg, Germany

[*] Notice: This patent issued on a continued prosecution application filed under 37 CFR 1.53(d), and is subject to the twenty year patent term provisions of 35 U.S.C. 154(a)(2).

[21] Appl. No.: 09/029,024

[22] PCT Filed: Aug. 21, 1996

[86] PCT No.: PCT/EP96/03685

§ 371 Date: Feb. 24, 1998

§ 102(e) Date: Feb. 24, 1998

[87] PCT Pub. No.: WO97/07754

PCT Pub. Date: Mar. 6, 1997

[30] Foreign Application Priority Data

Aug. 25, 1995 [DE] Germany .................. 295 13 694 U

[51] Int. Cl.[7] .................... A61F 2/32; A61F 2/36
[52] U.S. Cl. .................... 623/22.11; 623/23.11; 623/18.11
[58] Field of Search .................... 623/22, 16, 18, 623/23, 22.11, 23.11, 22.12–22.46, 23.12–23.26, 16.11, 18.11

[56] References Cited

U.S. PATENT DOCUMENTS

| 5,019,015 | 5/1991 | Wiley . | |
| 5,019,105 | 5/1991 | Wiley | 623/22 |
| 5,062,853 | 11/1991 | Forte | 623/22 |
| 5,222,984 | 6/1993 | Forte | 623/22 |
| 5,507,826 | 4/1996 | Besselink et al. | 623/22 |
| 5,549,693 | 8/1996 | Roux et al. | 623/22 |
| 5,725,589 | 3/1998 | Pfaff et al. | 623/22 |

FOREIGN PATENT DOCUMENTS

| 0 053 794 | 6/1982 | European Pat. Off. . |
| 0 285 756 | 10/1988 | European Pat. Off. . |
| 20 24 583 | 11/1970 | Germany . |
| 4337936 | 5/1995 | Germany . |

*Primary Examiner*—Mickey Yu
*Assistant Examiner*—Alvin Stewart
*Attorney, Agent, or Firm*—Morrison & Foerster LLP

[57] ABSTRACT

In an endoprosthesis including a ball-and-socket joint, the ball and a socket insert having a spherical surface are made of ceramic material. The opening edge of the socket is covered by a polyethylene protecting ring whose opening side is covered by a covering ring made of a resilient material. The inner edge of the protecting ring is appropriately covered by the protecting. The socket, the ceramic insert, the protective ring and the covering ring are configured so as to permit sliding of a ball seated in the socket and configured to conform to the spherical surface of said ceramic insert out of the endoprosthesis.

17 Claims, 1 Drawing Sheet

ENDOPROSTHESIS WITH A BALL-AND-SOCKET JOINT

It is known (EP-A 53794) to equip the socket of a ball-and-socket endoprosthesis, for example a hip prosthesis, with a slide surface which is made of ceramic material. If, in the event of so-called subluxation, the ball guided therein moves partially away from the intended bearing position, line contact with the edge of the slide surface may occur, which can lead to damage of both the ball and also the edge of the socket. It has thus been proposed to place a protective ring made of plastically deformable polyethylene in front of the edge of the slide surface (EP-A 53794).

This protective ring is not normally subject to any wear. However, it may happen that in the event of a strongly projecting movement, the neck carrying the ball will strike the polyethylene ring. This can lead to damaging friction. It has also been found that the protective ring may be deformed in the process, so that its function of protecting the ceramic part is impaired.

According to the invention, these disadvantages are avoided by the fact that the front side of the protective ring is covered by a covering ring made of resistant material. This material may be a metal or even a resistant plastic. To ensure that the surface of the ball cannot strike the covering ring and become damaged in the event of subluxation, the protective ring is expediently designed in such a way that it covers the inner edge of the covering ring.

Figure 2:
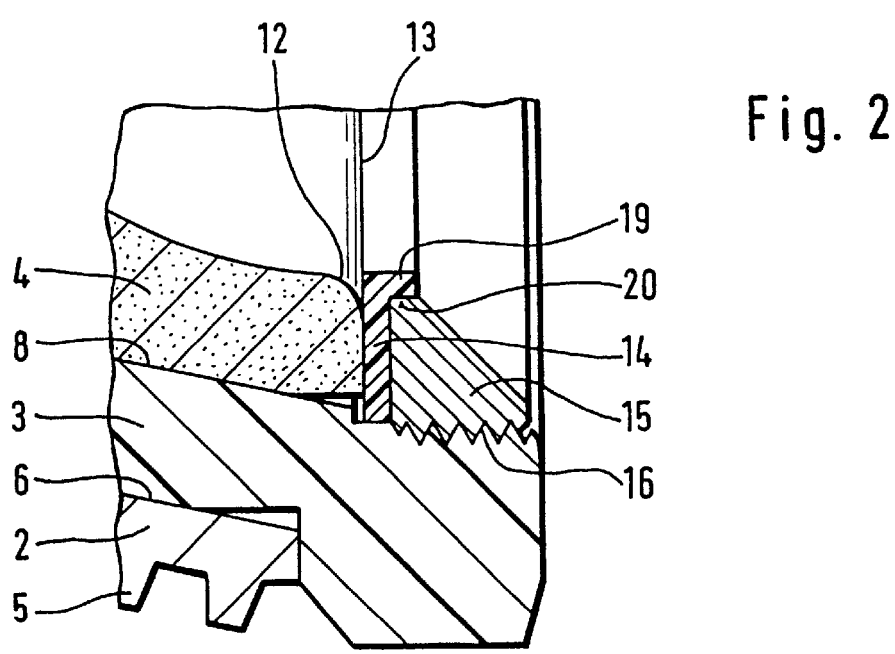

The invention is explained in greater detail hereinbelow, with reference being made to the drawing which depicts an advantageous illustrative embodiment and in which:

FIG. 1 shows an enlarged longitudinal section through a hip-joint endoprosthesis, and FIG. 2 shows a still further enlarged partial section through the edge of the socket.

The hip socket 1 comprises a holder 2, a polyethylene body 3 and a ceramic insert 4. The holder 2 is externally designed such that it can be anchored easily and permanently in the bone. For this purpose, it is provided, for example, with projections 5. For details of this, reference may be made to the prior art.

It has a frustoconical inner shape 6, 7 to which the outer shape of the polyethylene body 3 corresponds. After implantation of the holder 2, this outer shape can be fitted therein essentially free of play and anchored. This too is known.

The polyethylene body 3 has a frustoconical inner shape 8, 9 to which the outer shape of the ceramic insert 4 corresponds free of play, if appropriate with a slight oversize. This ceramic insert 4 consists of a physiologically compatible ceramic material which exhibits a high degree of resistance to wear, for example high-purity aluminium oxide ceramic. It forms a spherical slide surface 10 which corresponds to the spherical configuration of the ball 11 which is mounted therein. The spherical slide surface 10 extends in each direction over approximately 180°; the equator of the spherical surface forming the slide surface 10 lies somewhere between the start of the edge rounding 12 and the front side 13.

Applied to the front side 13 of the ceramic insert there is a protective ring 14 made of high-density polyethylene or similar resilient and preferably sufficiently elastic material, which ring 14 is in turn covered over a large extent by a covering ring 15 made of suitable material, for example titanium. In the example depicted, this covering ring 15 is designed as a threaded ring which cooperates with the polyethylene body 3 via a thread 16 in order to secure the ceramic insert 4 and the protective ring 14 in position. A securing means (not shown) can be provided in order to prevent undesired loosening of the covering ring 15.

The polyethylene body 3 transmits force in a uniformly distributed manner from the ceramic body 4 to the holder 2 and in this way protects against harmful stress concentrations on the ceramic body 4. Likewise, the protective ring 14 distributes the retaining force, originating from the covering ring 15, to the front side 13 of the ceramic body 4 while avoiding stress peaks.

The protective ring 14 preferably situated on the other side of the equator—as viewed from the slide surface 10 of the ceramic body 4—projects inwards almost to the imaginary spherical surface which continues the slide surface 10 on the opening side. On the one hand, it expediently has a little play with respect to the ball 11, when the latter is lying properly on the slide surface 10, so that frictional wear of the polyethylene is avoided and the joint fluid has free access to the slide gap. On the other hand, it is expedient if its internal diameter is a little smaller than the maximum diameter of the ball 11, in order to form a force barrier preventing the ball from sliding out of the socket. Most subluxations can be prevented in this way. However, the force barrier should be smaller than the force at which the ball 11 can detach from the cone 17 bearing it.

The covering ring 15 protects the protective ring 14 from possibly damaging impacts from the ball neck 18. Because of this protection, it can be produced with greatly reduced dimensions. Its thickness is, for example, of the order of one millimetre. On its inner edge it has a collar 19 which extends axially parallel outwards and which lies in front of the inner edge 20 of the covering ring 15 and so protects against the ball 11 coming into potentially damaging direct contact with the covering ring 15 which is made of harder material. As can be seen in FIG. 2, the collar 19 can even protrude slightly over the edge of the covering ring 15 on the opening side. This admittedly means that the neck 18 can strike against the collar 19, but this does not cause any damage as long as the latter can deflect elastically. Its elastic deflection is possible by virtue of the fact that a wedge-shaped gap opens between the opening-side edge rounding 12 of the ceramic insert and the protective ring 14, into which wedge-shaped gap the inner edge of the protective ring can deflect back elastically in such a

What is claimed is:

1. An endoprosthesis, comprising:
    a socket comprising a ceramic insert having a spherical slide surface and forming an opening edge;
    a protective ring made of a resilient material and covering said opening edge of said ceramic insert; and
    a covering ring provided on a front side of said protective ring and covering said protective ring,
        said socket, said ceramic insert, said protective ring and said covering ring being configured upon implantation and assembly so as to permit sliding out of said endoprosthesis of a ball seated in said socket just by pulling the ball from the socket, said ball being configured to conform to said spherical surface of said ceramic insert.

2. The endoprosthesis of claim 1, wherein said protective ring comprises polyethylene.

3. The endoprosthesis of claim 1, further comprising a collar between said protective ring and said ceramic insert.

4. The endoprosthesis of claim 3, wherein said collar extends axially outward.

5. The endoprosthesis of claim 3, wherein said collar protrudes over the covering ring.

6. The endoprosthesis of claim 1, wherein said covering ring comprises titanium.

7. An endoprosthesis, comprising:

a socket comprising a polyethylene body and a ceramic insert, said ceramic insert having a spherical slide surface and forming an opening edge;

a protective ring made of a resilient material and covering said opening edge of said ceramic insert; and a covering ring provided on a front side of said protective ring and covering said protective ring and cooperating with said polyethylene body, said socket, said ceramic insert, said protective ring and said covering ring being configured upon implantation and assembly so as to permit sliding out of said endoprosthesis of a ball seated in said socket just by pulling the ball from the socket, said ball being configured to conform to said spherical surface of said ceramic insert.

8. The endoprosthesis of claim 7, wherein said protective ring comprises polyethylene.

9. The endoprosthesis of claim 7, further comprising a collar between said protective ring and said ceramic insert.

10. The endoprosthesis of claim 9, wherein said collar extends axially outward.

11. The endoprosthesis of claim 9, wherein said collar protrudes over the covering ring.

12. The endoprosthesis of claim 7, wherein said covering ring comprises titanium.

13. An endoprosthesis comprising a ball and a socket having a slide surface formed by a ceramic insert in said socket, said ceramic insert comprising an opening edge; a protective ring in contact with said opening edge; and a covering ring covering a front side of said protective ring, said covering ring comprising an inner edge, said socket, said ceramic insert, said protective ring and said covering ring being configured upon implantation and assembly so as to permit sliding of said ball seated in said socket out of said socket just by pulling out the ball from said socket.

14. The endoprosthesis of claim 13, wherein said opening edge of said ceramic insert is rounded.

15. The endoprosthesis of claim 14, wherein said rounded edge forms a wedge-shaped region between said ceramic insert and said protective ring.

16. The endoprosthesis of claim 5, further comprising a ball mounted in said socket and having an outer surface configured to conform to said spherical slide surface.

17. The endoprosthesis of claim 7, wherein said covering ring engages with said polyethylene body via threads.

* * * * *